United States Patent
Teoh et al.

(10) Patent No.: US 8,968,352 B2
(45) Date of Patent: Mar. 3, 2015

(54) EXPANDABLE BODY CAVITY LINER DEVICE

(75) Inventors: Clifford Teoh, Los Altos, CA (US); Joseph C. Eder, Los Altos Hills, CA (US); Michael P. Wallace, Pleasanton, CA (US); Stephen C. Porter, Oakland, CA (US); David C. Barry, Livermore, CA (US); Amol Parkar, San Ramon, CA (US)

(73) Assignees: Stryker Corporation, Kalamazoo, MI (US); Stryker European Holdings I, LLC, Kalamazoo, MI (US)

(*) Notice: Subject to any disclaimer, the term of this patent is extended or adjusted under 35 U.S.C. 154(b) by 2593 days.

(21) Appl. No.: 10/631,928

(22) Filed: Jul. 31, 2003

(65) Prior Publication Data
US 2004/0098027 A1    May 20, 2004

Related U.S. Application Data

(62) Division of application No. 09/918,991, filed on Jul. 31, 2001, now abandoned.

(51) Int. Cl.
*A61M 29/00*    (2006.01)
*A61B 17/12*    (2006.01)

(52) U.S. Cl.
CPC ..... *A61B 17/12022* (2013.01); *A61B 17/12113* (2013.01); *A61B 17/12172* (2013.01)
USPC .......................................... 606/200; 623/1.11

(58) Field of Classification Search
USPC ......... 606/108, 190, 194, 198, 191, 192, 195, 606/200; 604/104, 107; 623/1.11, 1.2
See application file for complete search history.

(56) References Cited

U.S. PATENT DOCUMENTS

| | | | |
|---|---|---|---|
| 4,364,392 A | 12/1982 | Strother et al. | 128/325 |
| 4,705,517 A | 11/1987 | DiPisa, Jr. | 623/12 |
| 5,334,210 A | 8/1994 | Gianturco | 606/151 |
| 5,454,833 A | 10/1995 | Boussignac et al. | 606/213 |
| 5,522,822 A | 6/1996 | Phelps et al. | 606/151 |
| 5,527,337 A * | 6/1996 | Stack et al. | 606/198 |
| 5,645,558 A | 7/1997 | Horton | 606/191 |
| 5,916,235 A | 6/1999 | Guglielmi | 606/200 |
| 5,928,260 A * | 7/1999 | Chin et al. | 606/200 |
| 5,944,730 A * | 8/1999 | Nobles et al. | 606/151 |
| 6,344,048 B1 * | 2/2002 | Chin et al. | 606/200 |
| 6,346,117 B1 * | 2/2002 | Greenhalgh | 606/200 |
| 6,350,270 B1 | 2/2002 | Roue | 606/151 |
| 6,454,780 B1 * | 9/2002 | Wallace | 606/151 |

(Continued)

FOREIGN PATENT DOCUMENTS

| | | |
|---|---|---|
| EP | 0 358 767 | 1/1988 |
| EP | 0 882 428 A2 | 12/1998 |
| WO | WO 96/01591 | 1/1996 |

(Continued)

OTHER PUBLICATIONS

Office Action dated May 1, 2003, in association with U.S. Appl. No. 09/918,991, filed Jul. 31, 2001 (parent case).

(Continued)

*Primary Examiner* — Victor Nguyen
(74) *Attorney, Agent, or Firm* — Vista IP Law Group LLP

(57) ABSTRACT

The present invention is a method for treating aneurysms of various shapes and sizes.

16 Claims, 10 Drawing Sheets

(56) References Cited

U.S. PATENT DOCUMENTS

| | | | |
|---|---|---|---|
| 7,128,073 B1 * | 10/2006 | van der Burg et al. | 128/887 |
| 2003/0028209 A1 | 2/2003 | Teoh et al. | 606/191 |

FOREIGN PATENT DOCUMENTS

| WO | WO 97/26939 | 7/1997 |
|---|---|---|
| WO | WO 99/03404 | 1/1999 |
| WO | WO 99/05977 | 2/1999 |
| WO | WO 99/30640 | 6/1999 |
| WO | WO 99/42059 | 8/1999 |
| WO | WO 00/27292 | 5/2000 |

OTHER PUBLICATIONS

Office Action dated Aug. 27, 2003, in association with U.S. Appl. No. 09/918,991, filed Jul. 31, 2001 (parent case).

PCT International Search Report for PCT/US02/23529 (WO 03/011151), Applicant: SciMed Life Systems, Inc., Form PCT/ISA/210, dated Dec. 12, 2002 (8 pages).

* cited by examiner

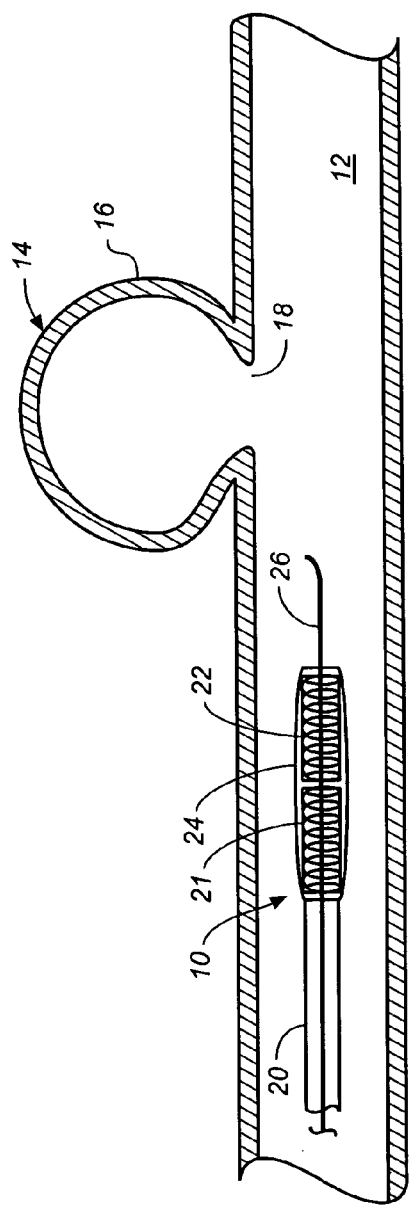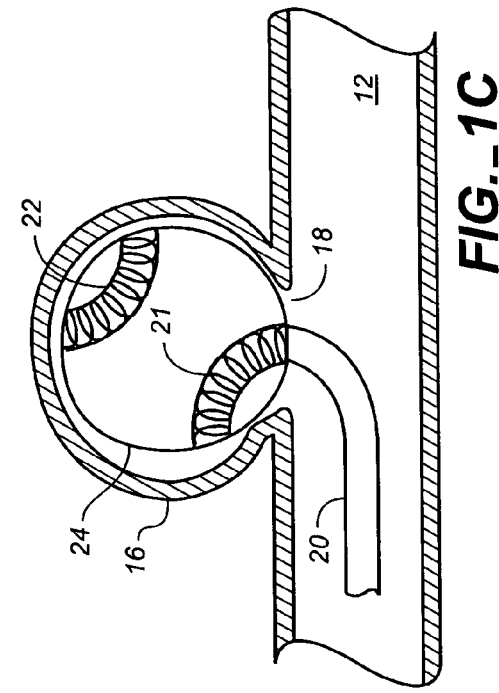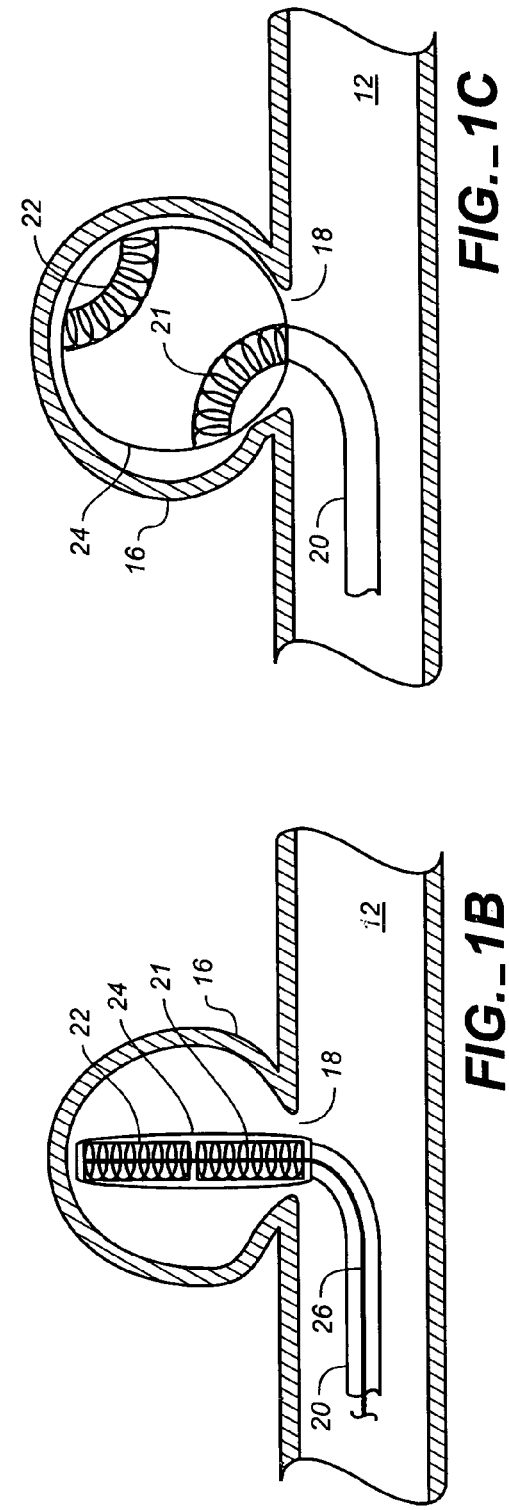

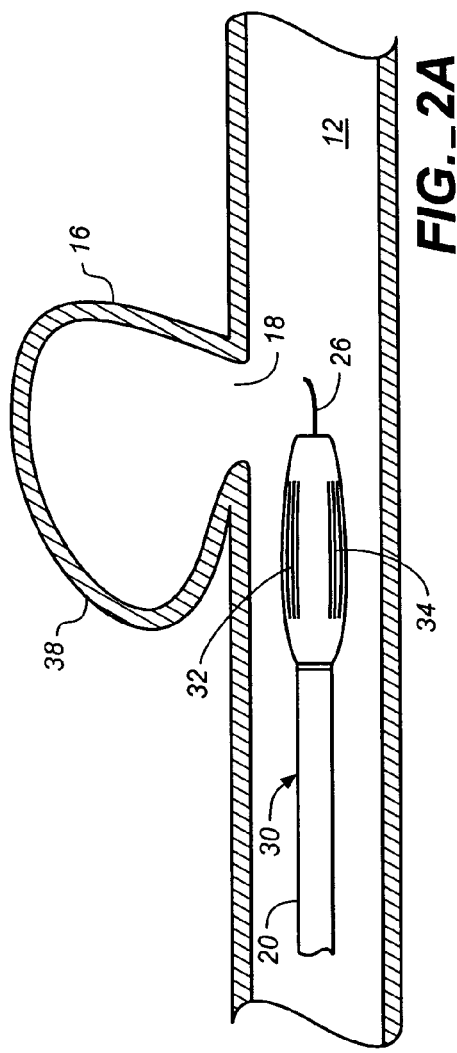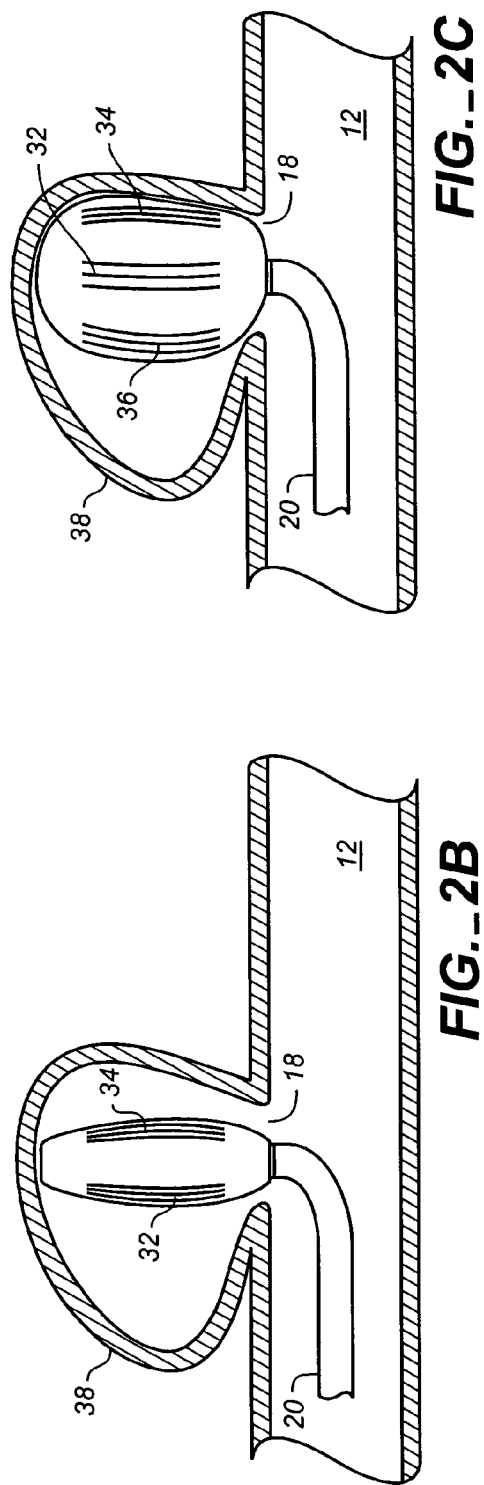

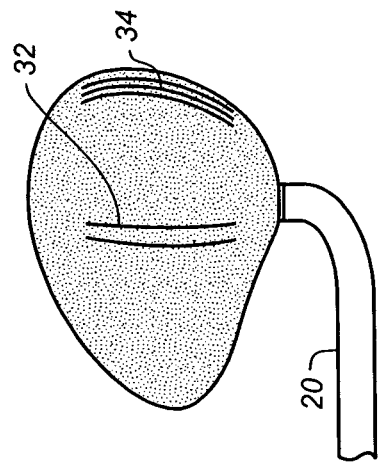
FIG._2E
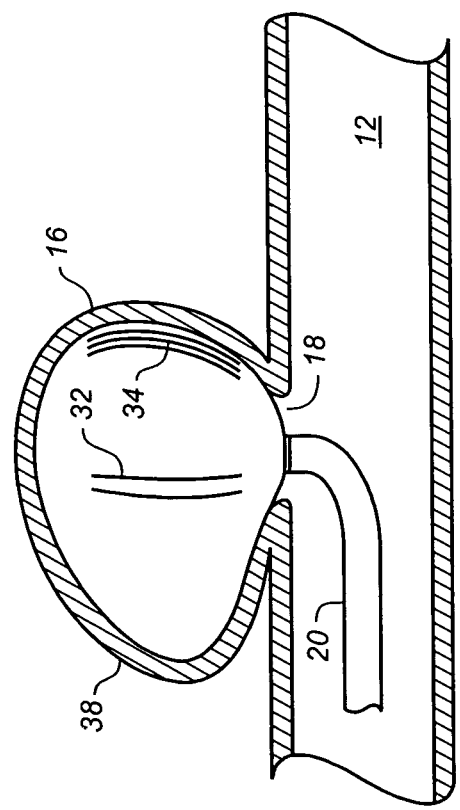
FIG._2D

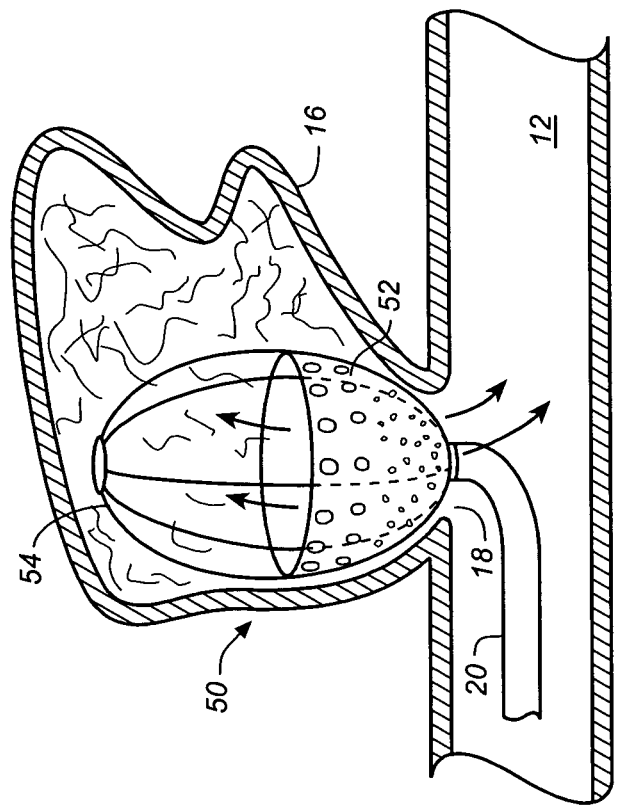
FIG._3B
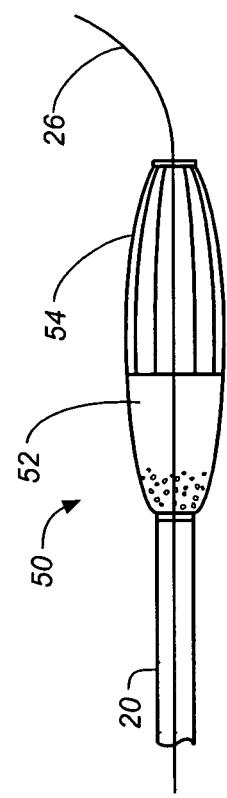
FIG._3A

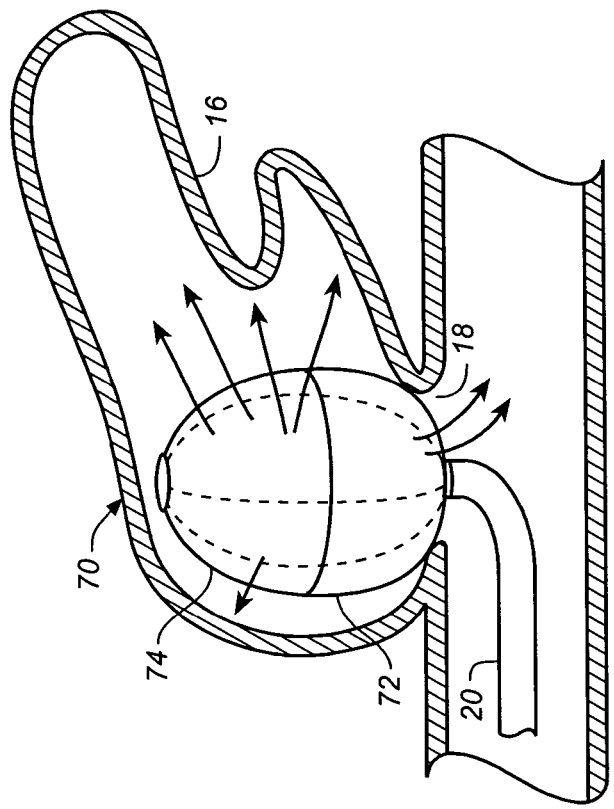
*FIG._5*
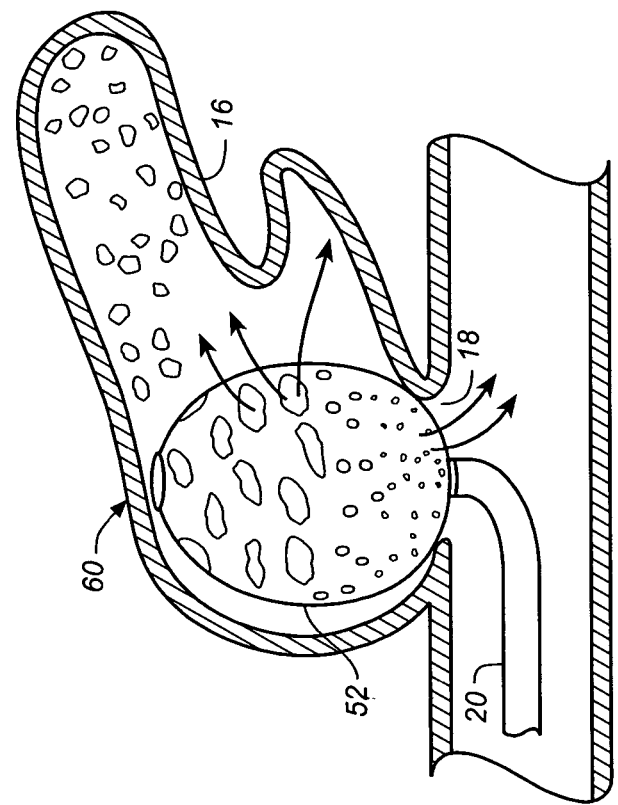
*FIG._4*

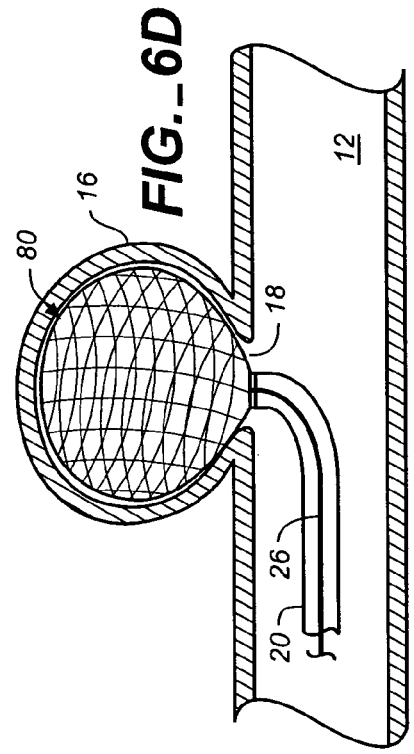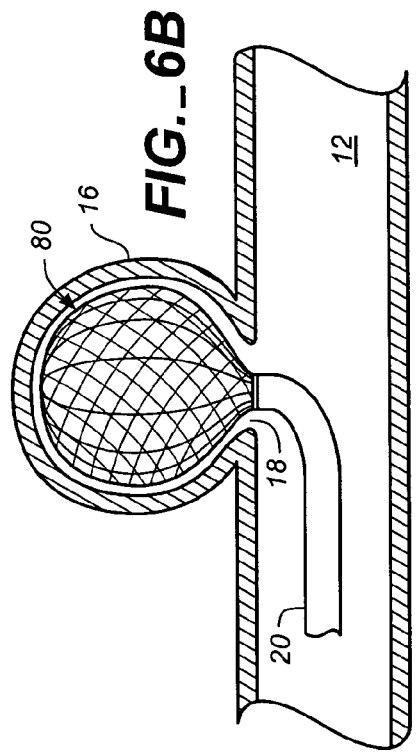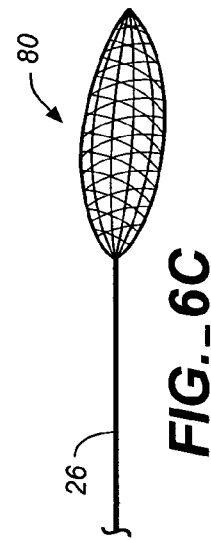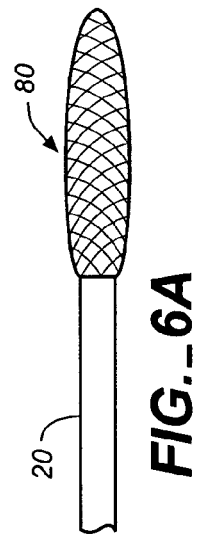

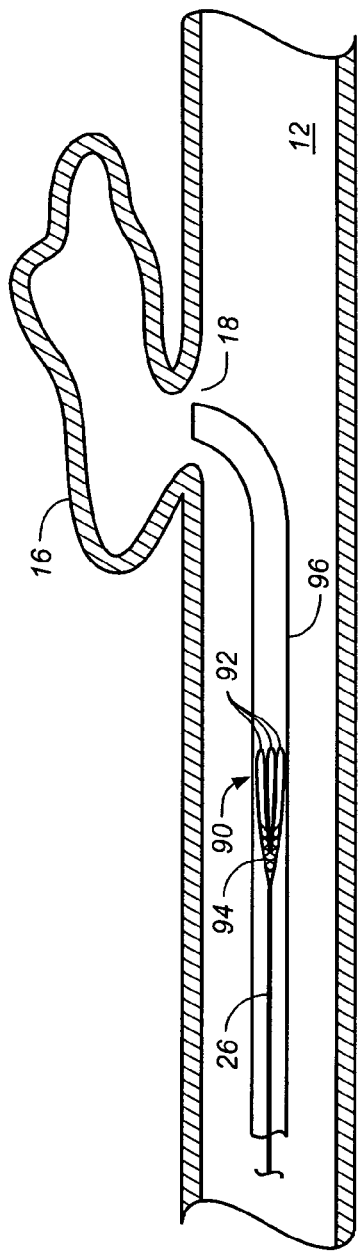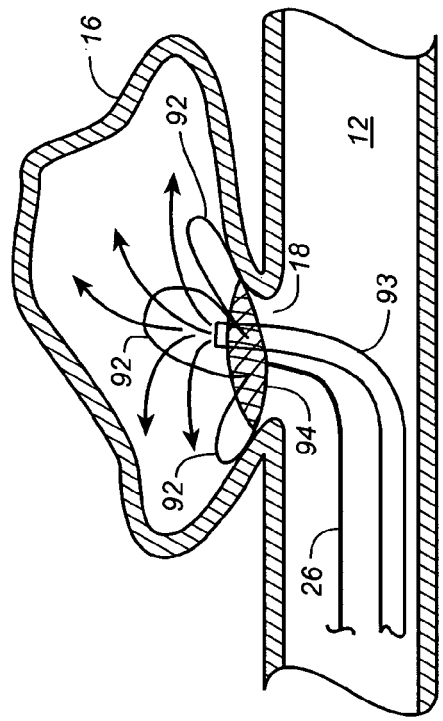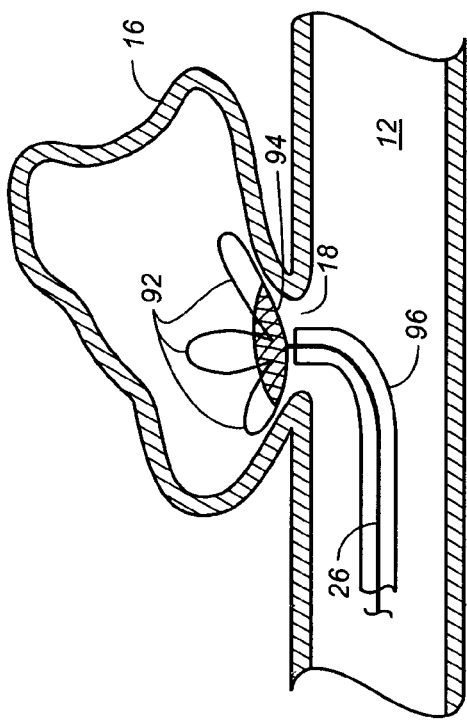

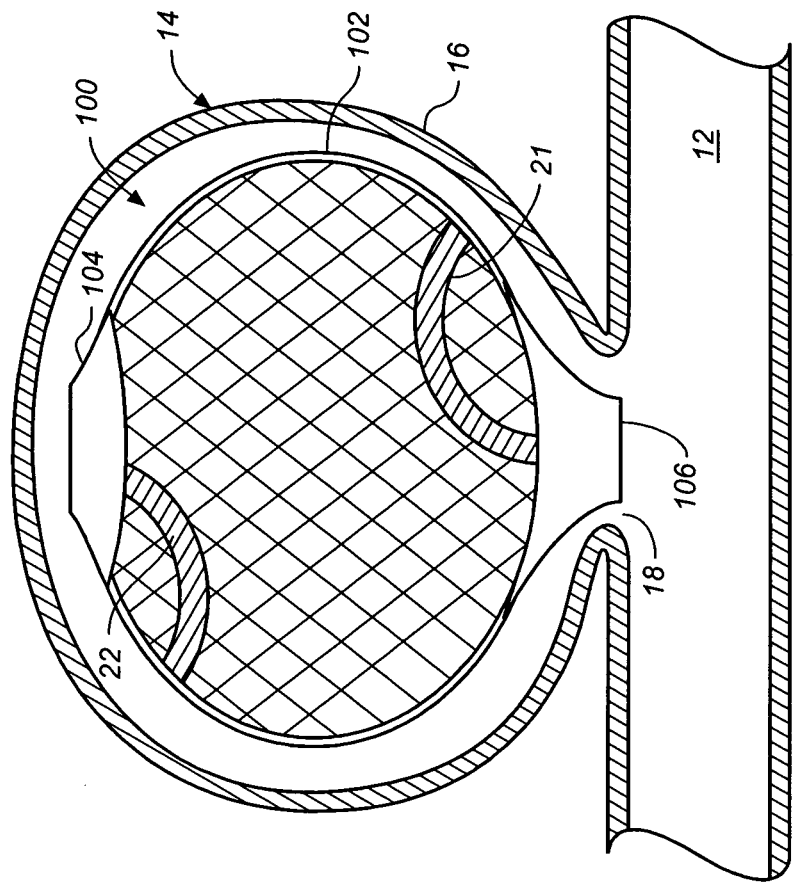
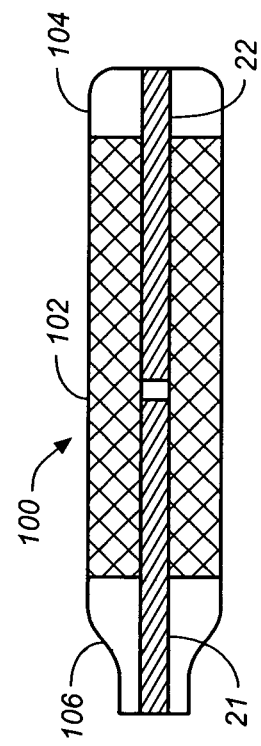
FIG._8B
FIG._8A

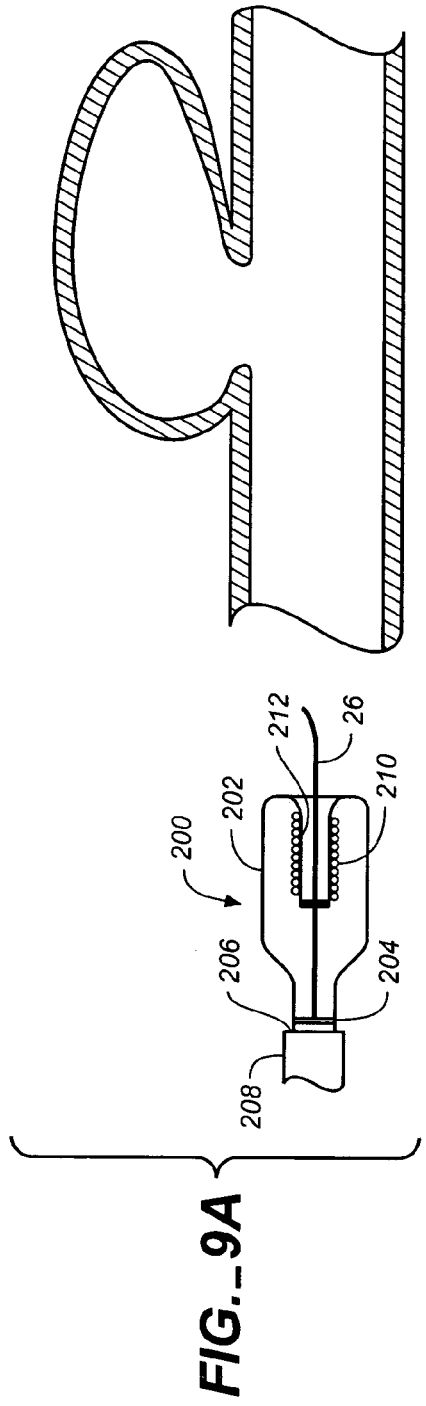
FIG._9A
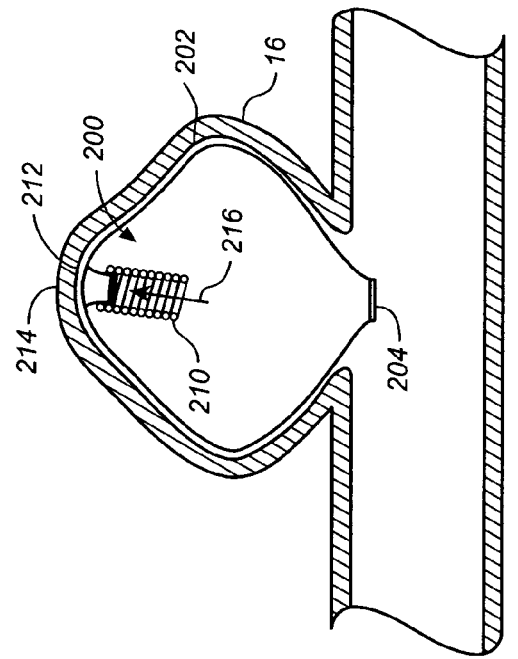
FIG._9C
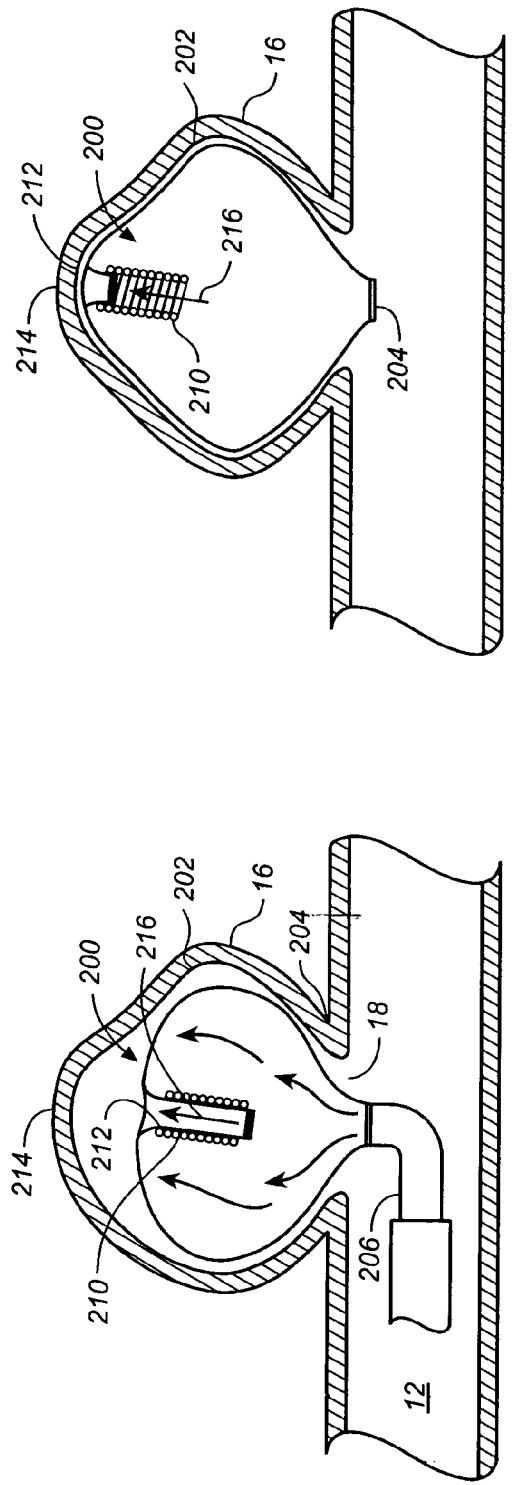
FIG._9B

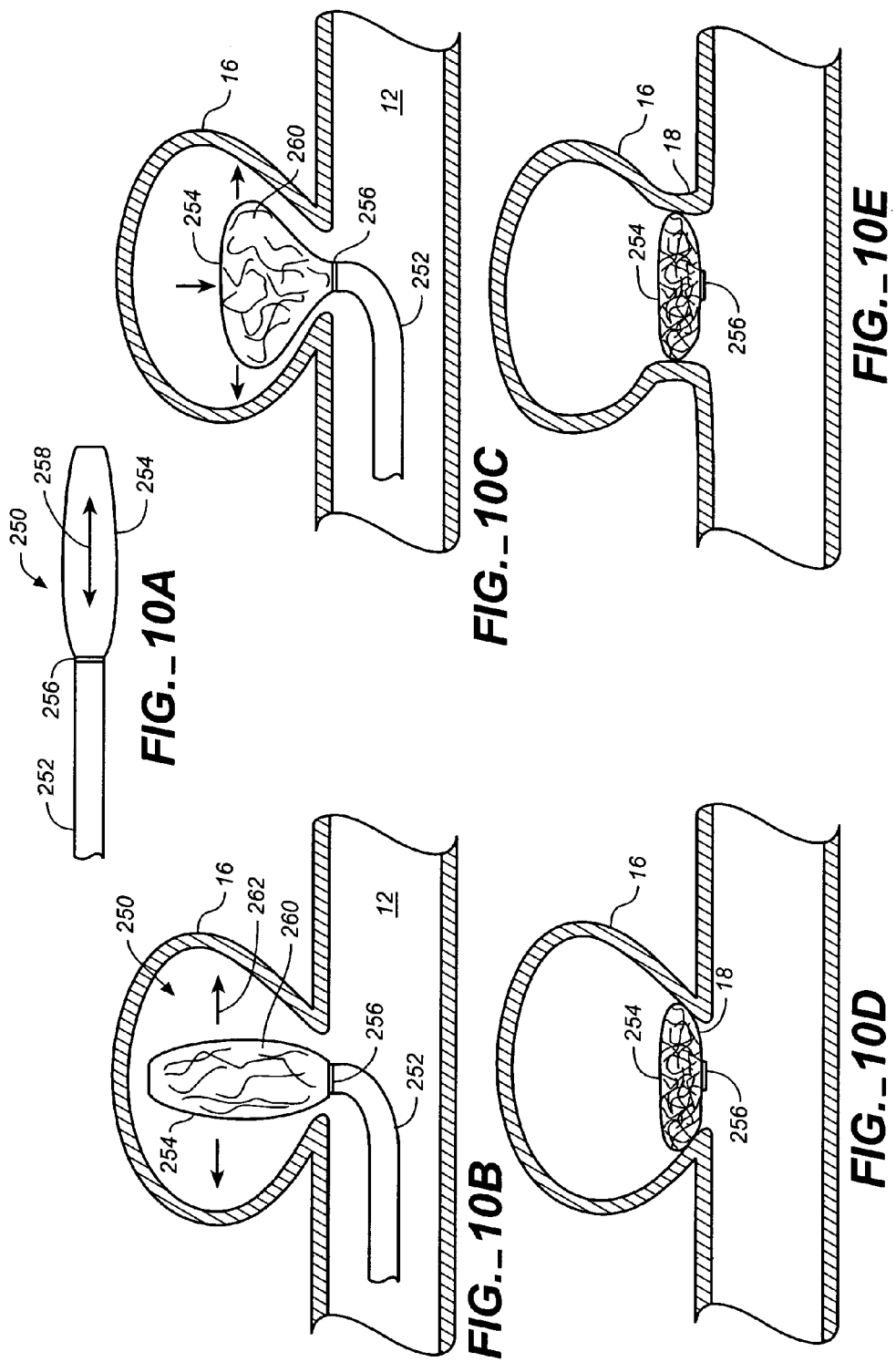

EXPANDABLE BODY CAVITY LINER DEVICE

The present application is a divisional of and claims priority of U.S. patent application Ser. No. 09/918,991, filed Jul. 31, 2001, the content of which is hereby incorporated by reference in its entirety.

BACKGROUND OF THE INVENTION

The present invention deals with a system for treating a vascular cavity. More specifically, the present invention is directed to vascular cavity liners and vascular cavity neck bridges.

While the present discussion proceeds with respect to aneurysms, it will be appreciated that it can be applied to other vascular cavities (such as vessels, lumens, etc.) as well. An aneurysm is a localized stretching or distension of an artery due to a weakening of the vessel wall. For example, "berry" aneurysms, i.e., small spherical distensions, occur in the vessels of the brain. The distension—often referred to as the aneurysm sac—is related to defects in the muscular coating of the artery and is probably degenerative in origin. Rupture of aneurysms account for the majority of spontaneous hemorrhages. Approximately 25,000 intracranial aneurysms rupture every year in North America.

Several methods of treating aneurysms have been attempted, with varying degrees of success. At present, the treatment of aneurysms with drugs is substantially ineffective. Also, extra-vascular surgery, referred to as open craniotomy, for the purpose of preserving the parent artery is replete with disadvantages. A patient subject to open craniotomy for intercranial aneurysms typically must undergo general anesthesia, surgical removal of part of the skull, brain retraction, dissection around the neck of the sac, and placement of a clip on the parent artery to prevent bleeding or rebleeding.

Alternative treatments include endovascular occlusion where the interior of the aneurysm is entered with a guidewire or a microcatheter. An occlusion is formed within the sac with an intention to preserve the parent artery. One means for forming a mass is through the introduction of an embolic agent within the sac. Examples of embolic agents include a detachable coil, which is detached from the end of a guidewire, a liquid polymer which polymerizes rapidly on contact with blood to form a firm mass, and embolic particles.

Endovascular occlusion is not without drawbacks. For example, there is a risk of overfilling the sac and consequent embolic agent migration into the parent vessel. Overfilling of the sac also generates additional pressure in the aneurysm.

Another means for forming a mass in the aneurysm sac involves the placement of an expandable balloon or liner in the aneurysm. Detachable occlusion balloons have been used for a number of medical procedures. These balloons are carried at the end of a catheter and, once inflated can be detached from the catheter. Such a balloon may be positioned within an aneurysm, filled and then detached from the catheter. Deploying the balloon within the aneurysm can be rather difficult due to the high rates of blood flow through the aneurysm. Elastic balloons have exhibited problems with respect to performance and have not been used endovascularly in some time.

This aneurysm filling technique also has its problems. As the balloon is filled, the operator must be very careful not to overfill the balloon due to possible risk of rupturing the aneurysm. Accordingly, the balloon may be too small, potentially resulting in the release of the balloon from the aneurysm into the blood stream. Furthermore, the balloon often does not mold or shape to the odd-shaped contours of the aneurysm leaving room for blood to continue flowing through the aneurysm, or generating undesired pressure on the aneurysm wall.

Aneurysm liners are composed of a permeable liner sac which is placed in the aneurysm and filled to occlude the aneurysm. A guidewire is inserted in the liner. The guidewire carries the liner through the vasculature to deploy the liner in the aneurysm.

All of the present systems for treating aneurysms have disadvantages as well. For example, while the aneurysm liner concept is intuitively attractive, it has posed a number of technical challenges. One primary challenge involves the difficulty in producing a material that is robust enough to contain embolic material without inhibiting the ability of the embolics to conform to the aneurysm geometry itself, rather than the geometry of the liner. For example, the elastic materials discussed above generally require to much force to deform, and inelastic materials that deform readily do not have adequate memory to conform to the aneurysmal wall.

Different types of aneurysms also present different challenges. For example, aneurysms which have a particularly wide opening between the aneurysm sac and the parent vessel ("wide neck aneurysms") present difficulties concerning the retention of embolic materials. Specifically, wide neck aneurysms make it very difficult to maintain the embolics, or occlusive materials, within the aneurysmal sac. This is especially true of liquid embolic materials. Of course, should the embolic material enter the parent vessel, it poses an undesirable risk of occlusion in the parent vessel.

Some current aneurysm liner concepts are inadequate in treating larger aneurysms. For example, some liner concepts involve forming the aneurysm liner of a woven or braided polymeric material such as polypropylene, polyester, nylon, urethane, teflon, etc. However, these mesh materials are difficult to use in treating aneurysms larger than, for example, twelve millimeters in diameter. Such mesh materials result in an assembly which is too bulky when collapsed down onto the catheter for delivery. In other words, the amount of materials required to fill a relatively large aneurysm is very difficult to collapse down into a constrained, low profile, delivery configuration small enough to be delivered and deployed without excess friction on the walls of the delivery catheter or other delivery lumen.

SUMMARY OF THE INVENTION

The present invention is a vascular cavity treatment device for treating vascular cavities of various shapes and sizes and will be discussed by way of example as an aneurysm treatment device.

In one embodiment, the aneurysm treatment device is formed as an aneurysm liner having portions folded over on itself when deployed at ambient internal pressure. However, when the pressure increases, the folded over portions unfold to increase the size of the aneurysm liner in the direction of unfilled portions of the aneurysmal sac.

The liner can be deployed using other means such as struts or shape memory polymer as well. The device itself can also be formed of shape memory polymer material.

In another embodiment, the aneurysm treatment device is formed to allow embolic material to preferentially exit the distal end of the aneurysm treatment device. This allows the embolic material to fill irregularly shaped portions of the aneurysm sac, without escaping though the neck of the aneurysmal sac.

In yet another embodiment, the present invention includes a shape memory polymer woven or braided with a density sufficient to inhibit movement of embolic material, once introduced into the liner, through the neck portion of the liner. Similarly, the shape memory polymer can be disposed on an aneurysm neck bridge.

BRIEF DESCRIPTION OF THE DRAWINGS

FIGS. 1A-1C illustrate the deployment of an aneurysm liner in an aneurysm.

FIGS. 2A-2D illustrate deployment of an aneurysm liner having folded or pleated portions that unfold into irregularly shaped areas of the aneurysm sac.

FIG. 2E shows the embodiment of an aneurysm liner illustrated in FIGS. 2A-2D with perforations therein.

FIGS. 3A and 3B illustrate an aneurysm treatment device which allows embolic material to preferentially exit the distal end thereof, wherein FIG. 3A shows the treatment device in a collapsed position and FIG. 3B shows the device in a deployed position.

FIGS. 4 and 5 illustrate two different embodiments of an aneurysm treatment device that allows embolic material to preferentially exit the distal end thereof.

FIGS. 6A-6D illustrate a shape memory polymer mesh aneurysm liner connected to a catheter (FIGS. 6A and 6B) and connected to a delivery wire (FIGS. 6C and 6D).

FIGS. 7A-7C illustrate an aneurysm treatment device that includes a shape memory polymer connected to a neck bridge device.

FIGS. 8A and 8B show an aneurysm treatment device made of a plurality of different materials.

FIGS. 9A-9C show another embodiment of the present invention.

FIGS. 10A-10D show still another embodiment of the present invention.

FIG. 10E shows the device of FIGS. 10A-10D in a small, or narrow, neck aneurysm.

DETAILED DESCRIPTION OF THE ILLUSTRATIVE EMBODIMENTS

FIGS. 1A-1C illustrate a portion of an aneurysm treatment device 10 in a vessel 12 which has an aneurysm 14 therein, and thus illustrate the general context of the present invention. Though the embodiments discussed herein are discussed in conjunction with an aneurysm, it will be appreciated that they can be used in substantially any vascular cavity. Aneurysm 14 is defined by aneurysmal sac 16 and neck 18. Device 10 includes, in the embodiment illustrated, delivery catheter 20, a pair of extender coils 21 and 22 and an expandable liner 24. Delivery catheter 20 has a proximal end that extends proximally to a position where it is manipulable by an operator. The distal end of catheter 20 is releaseably connected to the liner 24 and coil 21. Coils 21 and 22 can either be attached to the liner or catheter, or unattached.

When in the insertion position shown in FIG. 1A, coils 21 and 22 are axially aligned with one another, their length is sufficient to substantially hold liner 24 in a low profile position for insertion and manipulation within the vasculature. In one embodiment, coils 21 and 22 are axially aligned with one another and with catheter 20 through the use of a guidewire 26 which is disposed within the lumen of catheter 20, through coils 21 and 22 and liner 24, and out the distal end of coil 22 and liner 24. Coils 21 and 22 are held in an axially aligned conformation by guidewire 26 such that coils 21 and 22 substantially conform to the curvature of guidewire 26. Coils 21 and 22, rather than guidewire 26, can act to extend and even tension liner 24.

FIG. 1B shows that treatment device 10 has been positioned through vessel 12 and neck 18 into the sac 16 of aneurysm 14. Similar items are similarly numbered to those shown in FIG. 1A. In use, aneurysm treatment device 10 can be preloaded or back loaded onto guidewire 26. Guidewire 26 is manipulated through the vasculature from the entry site (such as the femoral artery) to the region of vessel 12 containing the aneurysm. The distal tip of guidewire 26 is advanced across the neck 18 of aneurysm 14 and into the aneurysm sac 16. This can be done using any desirable visualization technique. In one embodiment, catheter 20 is placed over guidewire 26 prior to positioning guidewire 26 in the vasculature, with several centimeters of guidewire 26 extending distal of the distal tip of catheter 20. Therefore, when the distal end of guidewire 26 has passed the aneurysm neck 18, catheter 20 is positioned just proximal of neck 18. Treatment device 10 is then advanced into the aneurysm sac 16.

In another embodiment, guidewire 26 is placed in the vasculature first. Once the distal end of guidewire 26 is moved past the aneurysm neck 18, into the aneurysm sac 16, catheter 20 is advanced over guidewire 26 such that the extender coils 21 and 22 are pushed distally along the guidewire by the catheter. 20 until the aneurysm treatment device 10 is in place in the aneurysm sac 16.

FIG. 1C illustrates treatment device 10 deployed in aneurysm sac 16 in accordance with one embodiment. Similar items are similarly numbered to those shown in FIGS. 1A and 1B. Once device 10 is substantially fully within aneurysm sac 16, guidewire 26 is retracted proximally, but liner 24 remains connected to delivery catheter 20. The distal end of delivery catheter 20 holds expandable liner 24 in position within the aneurysm sac 16 while expandable liner 24 is filled with embolics. Expansion of liner 24 occurs after the distal end of guidewire 26 is retracted from the coils 21 and 22.

As shown in FIG. 1C, once guidewire 26 has been retracted, coils 21 and 22 recoil away from axial alignment with one another toward the periphery of liner 24. In one illustrative embodiment, coils 21 and 22 are biased to extend in opposite directions to enhance deployment of, and expansion of, liner 24 within aneurysm sac 16. In another embodiment, one or more intermediate coils are aligned over guidewire 26, and, as guidewire 26 is retracted, the intermediate coil(s) fall away and float freely within the liner.

Embolic material can now be introduced into liner 24 through catheter 20 using substantially any desired method. Such methods include, for example, advancing coils or particles into liner 24, pushing the embolic material into catheter 20 with guidewire 26 completely removed, or infusing or injecting embolic material through catheter 20 into liner 24. Liner 24 is thus filled with a common embolic agent, such as detachable coils, particles, etc.

Once liner 24 is filled, it is unable to be removed through aneurysm neck 18. Therefore, it is released from delivery catheter 20 and delivery catheter 20 is removed from the treatment site. Detachment of liner 24 from catheter 20 can be accomplished using any desired method, such as using electrolytic detachment, traction-based detachment, or other mechanical, electrical, heat-based, magnetic, chemical or other detachment.

FIGS. 1A-1C illustrate that device 10 is configured for convenient treatment of aneurysm 14, and in particular, a generally symmetrically shaped aneurysm. However, asymmetrically shaped aneurysm sacs, or those having an otherwise irregular geometrical shape present other problems. For example, if aneurysm sac 16 had a cavity extending out one side thereof, it may be difficult for liner 24 to fill that portion of the aneurysm sac.

FIGS. 2A-2D illustrate another embodiment of an aneurysm treatment device 30 in accordance with another embodiment of the present invention. Device 30 is similar to device 10 in that it is illustratively connected to a delivery catheter 20 and has coils 21 and 22 disposed within a liner 24, and is configured for advancement over guidewire 26. However, in the embodiment illustrated in FIGS. 2A-2D, liner 24 is also provided with a plurality of expansion zones designated by numerals 32, 34 and 36 in the Figures. Expansion zones 32-36 help to enable liner 24 to fill asymmetric portions (irregular portions) of an aneurysm sac. For example, in FIGS. 2A-2D, aneurysm sac 16 has an asymmetric lobe 38. The expansion zones 32, 34 and 36 on aneurysm treatment device 30 enable it to more completely fill the asymmetrically shaped aneurysm sac 16.

FIG. 2A shows aneurysm treatment device 30 in vessel 12 located proximal to neck 18 of aneurysm sac 16. FIG. 2B shows aneurysm treatment device 30 disposed within aneurysm sac 16, still in its collapsed, insertion position.

FIG. 2C shows liner 24 expanded somewhat to a first peripheral dimension, in which none of the expansion zones 32, 34 or 36 have yet been expanded. It can be seen that, in this conformation, aneurysm liner 24 is illustratively a substantially symmetrically shaped aneurysm liner under a first internal pressure, only slightly elevated over ambient pressure. However, expansion zones 32, 34 and 36 enable liner 24 to expand in an asymmetrical fashion, when additional internal pressure (e.g., 0-5 atmospheres and illustratively greater than zero atmosphere and less than two atmosphere or in a range of approximately 1-2 atmospheres) is applied within liner 24.

In one illustrative embodiment, liner 24 is an inelastic polymer film (either with or without perforations or openings therein). Expansion zones 32, 34 and 36 are illustratively formed as accordion-like sections where the liner material 24 is pleated or folded over on itself, and is slightly biased in that position, but readily and permanently unravels or opens to conform to an aneurysm perimeter when exposed to minimal additional radial forces from internal pressure (e.g., 0-5 ATM and illustratively 0-2 ATM or 1-2 ATM). Such forces can be generated, for example, by the introduction of embolic coils or particles, liquid embolics, or other embolic materials into the interior of aneurysm liner 24.

For example, FIG. 2D shows that expansion zone 36 has totally expanded under increased internal pressure within liner 24. FIG. 2D also illustrates that expansion zone 32 has expanded partially, but expansion zone 34 remains unexpanded. This allows liner 24 to expand in an asymmetrical, or irregular geometry to fill the irregular lobe 38 of aneurysm sac 16. Catheter 20 is then detached and removed, leaving aneurysm liner 24 in place within aneurysm sac 16.

FIG. 2E illustrates another embodiment of treatment device 30, in which treatment device 30 has a plurality of perforations therein. Of course, the perforations can be made mechanically or through the use of laser drilling or any other desired mechanism or method of forming perforations. The perforations provide for efficient blood displacement in that they hold embolic material within liner 24, but allow blood previously residing in aneurysm sac 16 to exit through neck 18 as liner 24 is expanded to fill the aneurysm sac 16.

FIGS. 3A and 3B illustrate another embodiment of an aneurysm treatment device 50 in accordance with another embodiment of the present invention. FIG. 3A shows treatment device 50 in the collapsed, insertion position, while FIG. 3B shows it in the deployed position, having embolic material delivered thereto. In one illustrative embodiment, treatment device 50 includes an aneurysm liner portion 52 supported by a network of expandable struts 54. Struts 54 are illustratively super elastic alloys, such as nickel titanium (Nitinol), or shape memory polymers, which are connected to liner portion 52. While FIGS. 3A and 3B show struts 54 connected to the interior of liner portion 52, they could certainly be connected to the exterior portion thereof, by braiding or weaving them into the material of liner portion 52 or by utilizing adhesive, stitching, or other bonding, etc.

FIG. 3A shows that, in the collapsed position, struts 54 are substantially collapsed into a linear position, and they thus drive collapse of liner portion 52 around them as well. In another embodiment coils 21 and 22 can be used, as in previous embodiments, to hold device 50 in its collapsed position. In this low profile position, device 50 can be advanced into the aneurysm sac 16. In one illustrative embodiment, device 50 is maintained in its collapsed low profile position within a delivery catheter, or confined by delivery wire 26. Delivery wire 26 is advanced such that its distal tip is located within neck 18 of aneurysm sac 16. Device 50 is then extended past the distal end of delivery wire 26 and struts 54 self deploy. In doing that, struts 54 expand outwardly to the position shown in FIG. 3B, and thus deploy liner portion 52 outwardly as well.

Embolic material is then introduced through catheter 20 and through the interior of device 50. Since the distal portion of struts 54 are not covered by liner material, the embolic material being delivered occupies substantially the entire portion of aneurysm sac 16, no matter how irregular in shape it may be. Once the aneurysm sac 16 is filled with embolics, catheter 20 is detached from device 50 and device 50 remains within aneurysm sac 16. FIGS. 3A and 3B also show that liner portion 52 can have optional perforations therein to enhance the ability of blood to flow from within aneurysm sac 16 as the aneurysm sac 16 is being filled with embolic material. Such perforations are small enough to inhibit the flow of embolic material from aneurysm sac 16 into parent vessel 12. The distally located perforations may be larger than those located proximally to facilitate distal permeation of embolics, although this is optional.

FIGS. 4 and 5 illustrate additional embodiments of aneurysm treatment devices 60 and 70, respectively. Device 60 is similar to device 50 shown in FIGS. 3A and 3B, except that liner portion 52 extends to substantially cover struts 54. However, the distal end of liner material 52 is provided with apertures that are of sufficient size (or are distributed with sufficient density) to allow embolic material to escape therethrough while the proximal side of liner material 52 is provided with perforations which are sufficiently small to retain the embolic material therein. For example, spherical PVA embolics may traditionally be 500 microns in size and may be used to fill a conventional aneurysm liner. The distal portion of device 60 can thus be perforated with 750 micron holes whereas the proximal portion near the neck 18 of aneurysm sac 16 can illustratively be perforated with 350 micron sized, irregularly distributed, holes. Therefore, as the embolics are introduced into liner portion 52, they are sized to be able to escape the distal end thereof and or occupy the irregular spaces in the aneurysm sac 16, without escaping back into the parent vessel 12.

It should also be noted that the embodiments shown in FIGS. 3A-5 need not include separate struts but can instead be formed of the liner material which is simply thicker, harder or coated with a stiffer material. Similarly, if struts are used, they can be formed of a relatively stiff fabric material as well.

The device 70 in FIG. 5 is similar to device 60 in FIG. 4, except that liner portion 52 is actually formed of two portions, a proximal portion 72 and a distal portion 74, which are formed of materials having different characteristics from one another. Proximal portion 72 has material properties that allow permeation of blood therethrough, but not embolics. However, distal portion 74 has material properties that allow permeation of both blood and embolics therethrough. This allows the embolic materials, once introduced through catheter 20, to escape through distal liner portion 74 into the irregularly shaped lobes of the aneurysm sac 16. It also allows blood to exit the aneurysm sac 16 into the parent vessel, without also allowing the embolics to escape.

In one embodiment, the properties of proximal portion 72 physically obstruct passage of embolics therethrough. For example, portions 72 and 74 can be provided with holes of the same size. However, when portions 72 and 74 are wet with embolics, portion 72 illustratively swells to reduce the size of holes therein (or portion 74 shrinks to increase the size or the holes therein) so that blood can flow through both portions 72 and 74 but embolics can only pass through distal portion 74. The hole sizes can also be controlled using coatings. Coatings on different portions 72 and 74 can swell at different rates. Similarly, if the liner portions 72 and 74 are formed of braided material, the size of the holes can be controlled by the thickness of coatings used to coat the braid material. The hole size can also be controlled based on the braided pitch and tightness etc. . . .

It should also be noted that the embodiments shown in FIGS. 4 and 5 can be made using struts that do not self-deploy, or using no struts at all. In such an embodiment, the liner is expanded (or deployed) merely by introducing embolics therein.

FIGS. 6A-6D illustrate further embodiments in accordance with the present invention. FIGS. 6A and 6B show an aneurysm treatment device 80 attached to a catheter 20, much as the previous embodiments have been attached. FIGS. 6C and 6D show treatment device 80 attached to a guidewire. Device 80 is formed of a shape memory polymer that is weaved or braided to an appropriate mesh density. Such shape memory polymers can tolerate up to 300-500 percent elastic deformation.

In use, the shape memory polymer, once weaved or braided to its desired conformation, is cooled and compressed to its low profile position shown in FIGS. 6A and 6C. Once the device 80 is positioned within aneurysm sac 16 (as shown in FIGS. 6B and 6D) a warm bolus of fluid, such as saline, is injected to locally heat the environment of device 80. This increase in temperature causes the shape memory polymer to assume its relaxed shape, such as a sphere or other weaved or braided shape shown in FIGS. 6B or 6D. Because the shape memory polymers allow up to 300-500 percent elastic deformation, the expansion ratio (between its constrained and relaxed sizes) allows the device to be collapsed down to a small enough configuration to easily be manipulated within the vasculature, but to still be expanded sufficiently to fill fairly large aneurysms, even those in excess of 12 millimeters in diameter.

It should also be noted that heating the environment can be accomplished in any other desired way as well, such as maintaining the shape memory polymer in a cooled state through injection of cooled saline and then simply allowing body heat to warm the device, or generating heat by any electrical, magnetic, chemical or other means.

FIGS. 7A-7C illustrate yet another embodiment of an aneurysm treatment device 90 in accordance with an embodiment of the present invention. Treatment device 90 illustratively includes an aneurysm neck bridge element, for example, formed of loops 92 of nickel titanium or shape memory polymer material. The aneurysm neck bridge includes, at its proximal end, a woven or braided shape memory polymer liner section 94. The loops 92 are maintained in a low profile (or constrained) position within a delivery catheter 96 for delivery to the aneurysm treatment site.

In one illustrative embodiment, loops 92 are held in the constrained position by compressing shape memory polymer 94 into a constrained position. Then, device 90 is advanced through delivery catheter 96 into the aneurysm sac 16. After it has been advanced into the aneurysm sac, a warm bolus of fluid, such as saline, is injected through delivery catheter 96 to warm the local environment of shape memory polymer 94. This causes shape memory polymer 94 to assume its relaxed position allowing loops 92 to open into the neck bridging position shown in FIG. 7B. Because the loops 92 are held in their low profile position by the shape memory polymer material 94 during delivery, this reduces the tendency of the loops to "pop" or "spring" open and thus reduces the friction within catheter 96, and enhances the ability to place the device quickly and accurately. Device 90 can be placed in neck 18 and embolics can be delivered through catheter 96. FIG. 7C shows that aneurysm sac 16 can also be filled with embolics through a separate catheter 93 placed through mesh 94.

FIGS. 8A and 8B illustrate yet another embodiment of a treatment device (or liner) 100 in accordance with the present invention. FIG. 8A shows device 100 in its collapsed, delivery position while FIG. 8B shows device 100 in its deployed position. Treatment device 100 is formed of two different types of material at desired locations, based on the properties of the material. The composite treatment device 100 is constructed, illustratively, of an expandable fabric liner type material 102 which forms the bodice of liner 100 and a polymer material such as wound urethane which forms the ends or poles of liner 100. The fabric type material is illustratively a material that is suitable for creating a spun, wound, mesh, weave or braided fabric, such as nylon, polyethylene, polypropylene, polyglycolic acid material, polylactic acid material, etc.

Due to the excessive volume created by gathering such materials to create the poles 104 and 106 of device 100, these areas are illustratively constructed from thinner material that can be material pre-shaped into three dimensional forms. Such materials can include, for example, polymers such as urethane, which is flowable over the ends of bodice portion 102 to form the poles thereof. To form the poles, the bodice can be formed, or placed, over a mandrel and the pole material is flowed thereover or form a sandwich thereabout. The pole material can also be placed over marker pole coils to enhance manufacturability and fluoro-visibility. This eliminates the need to gather the bodice material and form pleats, which yields an undesirably large volume.

FIGS. 9A-9C illustrate yet another embodiment of the present invention. FIG. 9A is a side, partial sectional view of a treatment device 200. It should be noted that while device 200 is shown over a guidewire 26, it need not be delivered over a guidewire but can be delivered using any technique suitable to the task. Device 200 includes a liner portion 202, and a detachment zone 204. The detachment zone 204 is connected to a proximal catheter 206 which can optionally be delivered within a delivery catheter 208 or by wire 26 alone. Within liner portion 202 is a coil 210. Coil 210 has, received therein, a folded section 212 of liner portion 202. In other words, the distal portion of liner 202 is tucked within, and frictionally retained within, coil 210.

FIG. 9B shows device 200 being deployed within an aneurysm 16 that has a distal lobe 214. In an initial stage of deployment, device 200 is placed within aneurysm 16, across neck 18. Embolic material is then inserted into liner portion 202 which causes it to move radially outwardly to fill the outer sides of aneurysm 16. However, this still leaves the distal lobe 214 of aneurysm 16 unfilled. Continued pressure within liner portion 202, (by the introduction of additional embolics, for instance) causes folded portion 212 to unfold distally, or to move in the direction indicated by arrow 216, out from within coil 210.

This adds additional axial length to device 200 such that it can better fill the distal lobe 214 of aneurysm 16. This is better illustrated in FIG. 9C. It can be seen in FIG. 9C that a majority of the folded portion 212 has now unfolded to become exposed to the aneurysm wall and thus fill distal lobe 214 of aneurysm 16.

Coil 210 can illustratively simply be a floating coil, within liner portion 202, having portion 212 folded or tucked in its interior such that it frictionally engages and lightly holds folded portion 212 within its interior until the force of embolics introduced into liner portion 202 causes portion 212 to unfold in the distal direction. Alternatively, coil 210 can be adhesively engaged to the surface of folded portion 212, with a weak adhesive that dissolves or can be broken simply by the force of introducing embolic material into liner portion 202.

Once device 200 is deployed within aneurysm 16, it is detached at detachment zone 204 using any suitable detachment technique and the remainder of the system is withdrawn from the vasculature.

FIGS. 10A-10D illustrate another embodiment of the present invention. FIG. 10A illustrates a treatment device 250 for deployment in an aneurysm. Device 250 includes a catheter portion 252 and an aneurysm liner portion 254. In one illustrative embodiment, liner portion 254 is configured to expand radially, but to shrink axially, when internal pressure is created through, for example, the introduction of embolics therein. Thus, device 250 may be suitable to treating wide neck aneurysms. Liner portion 254 is illustratively attached to catheter 252 at detachment zone 256.

In one illustrative embodiment, liner portion 254 is constructed of a highly linear porous polymer such as ePTFE. The orientation of the polymer chain in liner portion 254 is along the length of the device as indicated by arrow 258. This orientation configures device 250 to distend radially as coils or other embolics are introduced into the liner portion 254. This radial expansion results in the device shrinking axially.

For example, FIG. 10B shows device 250 deployed within aneurysm 16. Embolics (such as coils 260) are being introduced into liner portion 254. It can be seen that liner portion 254 begins to expand radially in the direction indicated by arrows 262 and beings to shrink axially.

FIG. 10C illustrates further deployment of device 250 within aneurysm 16. Continued introduction of embolic material 260 within liner portion 254 causes a continued increase in the radial dimension of liner portion 254 and a continued reduction in the axial dimension of liner portion 254. Once liner portion 254 is filled to a desired extent with embolic material, it has expanded radially to such a dimension to bridge neck 18 of aneurysm 16. This is better indicated in FIG. 10D. Liner portion 254 is then detached from catheter 252 at detachment zone 256 and the remainder of the system is withdrawn from the vasculature. Of course, it should be noted that an additional microcatheter or other delivery device can be inserted into aneurysm 16 either prior to, or after deployment of liner portion 254. Additional embolics can be introduced distal of liner portion 254 to completely fill the aneurysm.

FIG. 10E shows device 250 deployed in a small neck aneurysm. It can be seen that device 250 may be particularly well suited to this type of aneurysm as it easily seals the neck 18.

It should also be noted, of course, that the embodiments shown in FIGS. 9A-10D can be provided with features of the other embodiments as well, such as perforations, internal deployment coils, expansion zones, different elasticity materials, etc.

It should further be noted that all of the embodiments discussed herein can optionally have biodegradable, cell growth enhancing material such as polyglycolic acid (PGA) or polylactic acid (PLA) disposed thereon in a region that will illustratively be deployed in a neck region of the aneurysm. Of course, other material or combinations of these materials may be used as well.

It can thus be seen that the present invention provides a number of different embodiments for treating aneurysms. These embodiments address many of the various deficiencies and disadvantages associated with prior aneurysm treatment devices.

Although the present invention has been described with reference to illustrative embodiments, workers skilled in the art will recognize that changes may be made in form and detail without departing from the spirit and scope of the invention.

What is claimed is:

1. A method of occluding an aneurysm, the aneurysm having a neck and a sac, the method comprising:
   delivering a liner into the aneurysm, the liner having a proximal portion and a distal portion, wherein the distal portion of the liner is more permeable than the proximal portion of the liner;
   allowing the liner to expand within the aneurysm to define a substantially spherical interior volume within the aneurysm, so that the proximal portion of the liner extends across the aneurysm neck and the distal portion of the liner is positioned within the aneurysm sac; and
   introducing embolics through an opening in the proximal portion of the liner into the substantially spherical interior volume of the liner, wherein the distal portion of the liner allows preferential permeation of the embolics from the substantially spherical liner interior volume into the sac of the aneurysm.

2. The method of claim 1, wherein the liner comprises a biodegradable and biocompatible material.

3. The method of claim 2, wherein the liner distal portion comprises a liner portion supported by struts.

4. The method of claim 1, wherein the liner proximal portion comprises a liner portion supported by expandable struts.

5. The method of claim 4, wherein the liner distal portion comprises the struts, free of any covering.

6. The method of claim 4, wherein the liner portion comprises a shape memory polymer material.

7. The method of claim 6, wherein allowing the liner to expand comprises actuating the shape memory polymer.

8. The method of claim 1, wherein the proximal liner portion inhibits permeation of embolics from the liner interior into a parent blood vessel.

9. The method of claim 1, wherein the delivering step is carried out using an elongated delivery member releasably connected to the liner.

10. An assembly for treating an aneurysm, the aneurysm having a neck and a sac, comprising:
   a liner having a proximal portion and a distal portion, and defining an substantially spherical interior volume within the proximal and distal portions; wherein the distal portion has perforations sized to permeate embolics and is more permeable than the proximal portion, such that the distal portion preferentially permeates embolics from the substantially spherical interior volume into the aneurysm sac, and an elongated delivery member releasably connected to the liner.

11. The aneurysm treatment assembly of claim 10, wherein the liner is comprised of a biodegradable and biocompatible material.

12. The aneurysm treatment assembly of claim 10, wherein the liner proximal portion has perforations sized to permeate blood but to inhibit permeation of embolics.

13. The aneurysm treatment assembly of claim 10, wherein the liner proximal portion comprises a liner portion supported by expandable struts.

14. The aneurysm treatment assembly of claim 13, wherein the liner portion comprises a shape memory polymer material.

15. The aneurysm treatment assembly of claim 14, wherein the shape memory polymer is actuable between a low profile delivery configuration in which the liner confines the struts to a low profile configuration, and a relaxed, expanded configuration.

16. The aneurysm treatment assembly of claim 10, wherein the liner distal portion is comprised of a liner supported by expandable struts.

* * * * *